United States Patent [19]

Piron et al.

[11] Patent Number: 4,883,479

[45] Date of Patent: Nov. 28, 1989

[54] ABSORBENT NAPKIN, PARTICULARLY FOR INFANT'S DIAPER PADS

[75] Inventors: Jean P. Piron, Thoissey; Jean C. Daugan, Bougival, both of France

[73] Assignee: Colgate-Palmolive Company, New York, N.Y.

[21] Appl. No.: 912,759

[22] Filed: Sep. 26, 1986

[51] Int. Cl.⁴ .............................................. A61F 13/16
[52] U.S. Cl. ...................... 604/365; 604/370; 604/375; 604/379; 604/385.1
[58] Field of Search .............. 604/365, 370, 374, 375, 604/378, 379, 385

[56] References Cited

U.S. PATENT DOCUMENTS

| | | | |
|---|---|---|---|
| 3,294,091 | 12/1966 | Morse | 604/365 |
| 3,339,550 | 9/1967 | Van Haaften | 604/365 |
| 3,526,538 | 9/1970 | Lindermann et al. | 604/365 |
| 3,597,306 | 8/1971 | Mesek et al. | 604/365 |
| 3,606,887 | 9/1971 | Roeder | 604/365 |
| 3,667,468 | 6/1972 | Nystrand et al. | 604/365 |
| 3,683,916 | 8/1972 | Mesek et al. | 604/365 |
| 3,862,877 | 1/1975 | Camden | 604/365 |
| 3,913,580 | 10/1975 | Ginocchio | 604/374 |
| 3,921,639 | 11/1975 | Cepuritis | 604/365 |
| 4,216,773 | 8/1980 | Ryan | 604/365 |
| 4,624,666 | 11/1986 | DeRossett et al. | 604/365 |

FOREIGN PATENT DOCUMENTS 0803635 10/1958 United Kingdom ................ 604/365

Primary Examiner—C. Fred Rosenbaum
Assistant Examiner—Mark F. Colosimo
Attorney, Agent, or Firm—M. M. Grill; N. Blumenkopf

[57] ABSTRACT

An absorbent article comprising a base sheet of fluid impervious material, a top sheet of fluid pervious nonwoven material, and an absorbent pad disposed between the top sheet and the base sheet. The top sheet is secured to the base sheet along the periphery thereof. The absorbent pad has a central portion and two side panels folded under the top sheet and over the central panel. A binder secures the side panels to the central panel to render the central panel more absorbent.

4 Claims, 1 Drawing Sheet

ABSORBENT NAPKIN, PARTICULARLY FOR INFANT'S DIAPER PADS

The present invention relates to absorbent napkins of fibrous material, such as defibered woodpulp and particularly for use as absorbant pads for liquid excrements in an infant's diaper or napkin.

The latter generally includes an impermeable support sheet, for example of polyethylene, and an inner sheet permeable to the penetration of urine, for example non-woven material or a perforated film of plastics material, these sheets being connected to one another at their periphery and an absorbant pad is provided between the latter to absorb the liquid excrement. According to the type of diaper, this pad may be rectangular or may have a cut-out at the level of the crotch in a so-called anatomical shaped diaper.

The material generally used to form the absorbant pads is defibered woodpulp in sheet form. The latter can comprise a single layer of fibrous material and have a rectangular shape or be cut away at the crotch. The napkin can comprise two layers of fibrous material superimposed on one another, and these layers may have an identical thickness and/or different weight per unit area. In these double-layer napkins, one of the layers is generally of rectangular shape, the other being sometimes cut-out at the crotch.

The napkin can also be shaped, that is to say have volume of absorbant material greater at the center than at the side portions, such napkins being generally cut-out at the crotch. Simple rectangular napkins are also to be had which are folded back over the central portion so as to be C-shaped in cross-section. Such napkins possess poor mechanical properties to the extent that the fibrous material constituting them does not have the coherence necessary to stay in the form of an approximately homogenous napkin and has a tendency to crumb formation or decomposition into small balls.

To try to overcome this drawback, an attempt has been made to increase the cohesion of the napkin by compressing the latter over particular areas, for example by stamping or rolling, to form crossbraces. This method is, in fact, only a palliative which does not provide means for increasing the cohesion of the napkin the latter only showing, in fact, portions of higher density where the fibers have a tendency to be more integral with one another than in the portions of lower density. The presence of such high density areas has the drawback of substantially reducing the absorbant capacity of the napkin.

An attempt has also been made to improve the cohesion of napkins by the introduction of a permeable and strong sheet, for example a non-woven sheet, a sheet of cellulose wadding, or a thread, either in the folds of the napkins when the latter are folded, or between two neighboring layers when these napkins have several layers. The strong and impermeable sheet has also been used by simply enveloping the napkin. If the presence of such a sheet confines to a certain extent the napkin within a limited volume, it does not succeed in improving the mechanical characteristics, in that the fibrous material always shows a deficient cohesion in having always a tendency to crumb-formation or to be reduced to small balls or to become turn when it is worn by a user whose repeated movements distort the napkin. This leads to the creation of preferential paths through which the liquid flows directly without being trapped by the absorbant mass.

This degradation of the absorbant material can occur before micturition, which uses beforehand the absorption capacities of the napkin. However, more often still, this degradation is facilitated after a first urination, which considerably reduces the possibilities of absorption of a second urination.

The fibrous material of certain napkins may be associated with a powered material based on polymers, commonly called "superabsorbant", for example a polyacrylate. This powder may be dispersed in the mass of the fibers of the napkin, dusted over the surface of the napkin, dusted between two neighboring layers of napkin having several layers or even dusted on the inside of the fold of a napkin having such a fold. The powder not being fixed to the fibrous material, the latter has a tendency to agglomerate in the free areas of the infant diaper, which considerably reduces the possibilities of absorption that could be expected from incorporating such a "superabsorbant" agent.

It is an object of the present invention to overcome these drawbacks by providing an absorbant napkin based on a fibrous material which has very good cohesion so as to remain stable when it is worn by a user before or after a first urination while preserving good absorption capacities.

It is another object of the invention to provide a napkin comprising a powdered absorbant material fixed to the mass of the napkin.

For this purpose it is an object of the invention to provide a napkin of the aforesaid type, characterised in that it comprises means for increasing its cohesion.

According to other features: the means for increasing the cohesion comprise a flexible and adherent binder which extends over at least a part of the area of the napkin.

It is also an object of the invention to provide a method of manufacture of an absorbant napkin based on a fibrous material with reinforced cohesion, for example of defibered woodpulp, characterised in that over a central portion of the napkin comprised between two lateral portions is sprayed a flexible and adherent binder and in that each of the lateral portions is folded back onto the central portion, the binder fixing these lateral portions to the central portion.

The invention will be better understood on reading the description which follows of different embodiments given by way of examples and referring to the accompanying drawings, in which.

Figure 1:
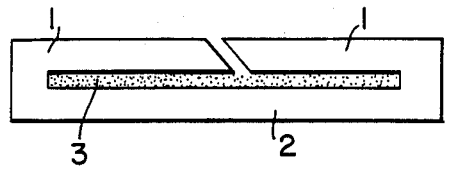
FIG. 1 is a diagramatic view in cross section of a folded napkin, a binder being provided inside the fold to increase the cohesion of this napkin.

By incorporating a binder in the napkin, the fibers of the latter are bonded in the region where the binder extends, similarly to the fibers of an unwoven fabric.

The binder may be deposited on at least one of the outer surfaces of the napkin of which both the lateral portions 1 are folded back onto a central portion 2 (FIG. 1), the binder 3 fixing these lateral portions 1 by gluing to the central portion 2. The binder may also be deposited between two layers 4 of a napkin comprising 2 layers (FIG. 2).

The binder may be deposited by spraying or by application in the form of spots, strips or filaments. In all cases, the binder has to form over the area of the napkin at the level at which it extends, free spaces so as to permit the liquid excrements to pass through the layer of binder to become distributed within the whole of the absorbant mass of the napkin.

The binder must be solid, flexible and adherent to bond the fibers together whilst permitting the napkin to be deformed. At the moment of its deposition on the napkin, the binder must have however a sufficiently fluid consistency so as to penetrate into at least a portion of the thickness of this napkin and impregnate the fibers therein.

Figure 2:
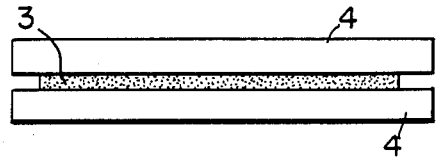
FIG. 2 is a diagramatic view in cross section of a napkin composed of two layers between which a binder has been provided to reinforce the cohesion of this napkin.

In the case of a folded napkin, such as that illustrated in FIG. 1, or of a napkin with two layers, such as that illustrated in FIG. 2, the binder 3 has been deposited respectively, on the unfolded layer and over an area of one of the layers of the napkin so that in refolding it, for one of the lateral portions 1 on the central portion 2 and by arranging for the other, the second layer of the napkin on the surface of the first layer on which the binder has been deposited, the different parts of the napkin are joined by gluing by means of the binder. The latter penetrates also into at least a portion of the thickness of the neighboring parts of the napkin, that is to say into the thickness of the lateral portions 1 and of the central portion 2 or within the thickness of the two layers 4 of the napkin.

The binder may be selected from among the following different materials;

a thermofusible glue, for example formed from an adhesive resin, a polymer and a wax, deposited hot in filaments or by spraying;

a cold glue, for example an acrylic or vinyl, used as an emulsion in water and sprayed. On evaporation of the water, there is coalescence of the droplets of glue in the emulsion which then forms a film providing free spaces over the sprayed surface;

a cold glue solubilised in an organic solvent and sprayed;

a polymer extruded or hot-sprayed, for example of polyethylene or polypropylene; and a polymer thread, for example of polypropylene or of polyethylene, or of thermofusible glue, this thread being melted directly on the layer to ensure the cohesion thereof.

It is also possible to associate with the fibrous material of the layer which constitutes the basic or preponderant absorbant portion of this napkin, an absorbant material which will advantageously be dusted on the freshly deposited binder so that this powder is immobilised on the layer by means of the binder.

Figure 3:
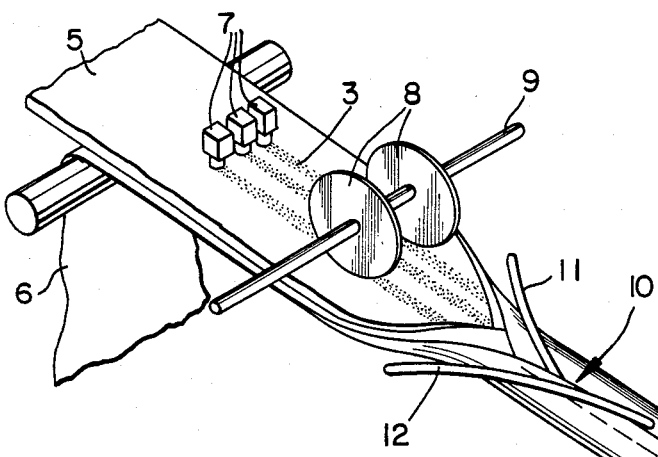
FIG. 3 is a diagramatic view of an installation for practising the method of the invention.

A description will now be given with reference to FIG. 3 of the method of manufacturing the absorbant napkin with reinforced cohesion, according to the invention.

This method is intended for the manufacture of napkins of the type of that of FIG. 1 which comprises two lateral portions 1 folded back onto the central portion 2 by being glued thereto by the central portion 2 by being glued thereto by means of the previously sprayed binder 3. A strip 5 of fibrous material, for example of defibered woodpulp, and a strong support sheet 5, for example of wadding, of width of the most corresponding to that of the strip 5, are led whilst superimposed on one another so as to pass under three binder spraying nozzles 7, the strip 5 extending opposite the nozzles 7 so that the latter deposit the binder only on the central portion of the strip.

Once coated with binder, the strip 5 supported on the sheet 6 passes into a folding device designed to fold the lateral portions of the strip 5 and of the sheet 6 onto the central portion of the strip 5, the lateral portions 1 of the strip 5 then being fixed by gluing to the central portion 2 of this strip by means of the freshly deposited binder.

The folding device comprises two discs 8 movably mounted in rotation on a shaft 9 which extends transversely above the strip 5, the discs 8 being applied to the surface of the strip 5 and being spaced axially on the shaft 9 so that the distance to which they are spaced from one another corresponds approximately to the width of the central portion of the strip 5 on which the binder is deposited. The folding device also comprises a backfolding fork 10 downstream of the disc 8 so that when the strip 5 and the strip 6 advance, this fork 10 folds back the lateral portions of the latter over the central portion of the strip. The discs 8 are for the purpose of preventing these lateral portions from folding back onto the strip before the passage of the fork, each lateral portion coming into abutment against the outer surface of the corresponding disc 8 to thus oblige the strip 5 to be held spread out beneath the nozzles 7 positioned upstream of the discs 8.

The fork 10 comprises two prongs 11 and 12 independent of one another forming a V open in the direction of the nozzle 7, each prong folding beneath it a corresponding lateral edge of the strip 5 and of the sheet 6. For this purpose, one prong 12 is positioned above the other prong 11 by being spaced from the latter so that the corresponding lateral edges of the strip 5 and of the sheet 6 with which this prong 12 cooperates, may be able to pass between the latter and the prong 11.

The assembly formed by the strip 5 and the sheet 6 can then be cut up at regular intervals along its length to provide the required absorbant napkins. If desired, the latter may be cut up at the level of the crotch (FIG. 5), in a so-called anatomic shape.

Figure 4:
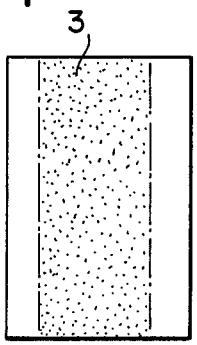
FIGS. 4 and 5 are diagramatic views in plan view, respectively of a rectangular napkin and of a napkin with a cut-out crotch, illustrating the area of the napkin over which the binder is spread.
Figure 5:
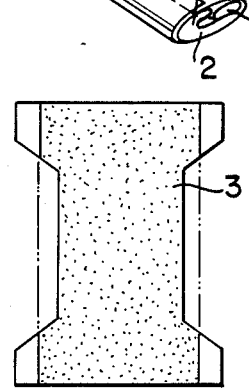

The central portion of the napkin over which the binder extends must of course be as wide as possible but for the problems posed by the guiding of the strip from which the napkin has resulted in the course of its manufacture, the portion of the surface over which the binder extends, presents at a maximum about 80% of the total surface of the napkin (FIGS. 4 and 5).

Experience shows also that so that the effectiveness of the binder is not compromised on an anatomical shaped napkin, the width of the area of the latter over which the binder extends at the level of the crotch must represent at the minimum 50% approximately of the width of the napkin at the level of this crotch.

Below are given experimental examples intended to illustrate the considerable adhesion of the napkins of the invention as well as their notable absorption power.

Tests of tear resistance measured by means of a dynamometer were carried out on napkins of defibered woodpulp identical in section and in weight per unit surface at a traction speed of 100 mm per minute. The results are indicated in Table 1 below for three different binders deposited in variable amounts with respect to a control napkin constituted only of defibered woodpulp.

Perforation strength tests were also carried out on the same napkins tested previously, by perforating by means of a metal cane with a hemispherical end and of 25 mm diameter with a perforation speed of 300 mm per minute, the perforation strength being measured by means of a compression dynamometer. The results are indicated in Table 1 below.

An evaluation test of their intrinsic absorption capacity was also carried out on a series of napkins identical with those previously tested, that is to say the value of the absorption obtained by dipping these napkins horizontally into a liquid so that under these conditions, the pressure exerted by the liquid absorbed inside the napkin has only negligible influence on the absorption capacity of the latter.

TABLE 1

|  | Tear* Strength + (N) | Perforation* Resistance + (N) | Intrinsic* Absorption + (g/g) ++ |
|---|---|---|---|
| Napkin of pure defibered woodpulp | 0.9 | 2.0 | 12.4 |
| Napkin of defibered woodpulp with increase in the cohesion by a thermofusible glue: | | | |
| N° 1 about 10 g/m² | 5.7 | 7.2 | 11.7 |
| about 20 g/m² | 8.0 | 18.3 | 12.5 |
| N° 2 about 10 g/m² | 3.0 | 10.5 | 11.6 |
| about 20 g/m² | 4.0 | 9.5 | 11.1 |
| For an acrylic glue: | | | |
| about 10 g/m² | 5.6 | 8.2 | — |
| about 20 g/m² | 7.8 | 13.1 | 11.8 |

*Average result of ten tests.
++ These values are not significantly different

These results show the substantial improvement in the cohesion of the napkins of the invention.

The increase in the cohesion of a napkin with a binder does not in fact diminish significantly the space between the fibers of the latter and hence the absorption capacity, which is exactly the reverse of the results obtained with the napkins of which certain regions have been compressed to increase the cohesion thereof.

Below are given the results of experimental tests to determine the effective absorption capacity, that is to say before rupture, of napkins based on defibered woodpulp of comparable cross sections and mass per unit surface. This experiment is a comparison of the effective absorption capacity of napkins with different binders and the different amounts of binder with respect to a napkin of pure defibered woodpulp.

The experimental conditions used were for the purpose of imitating the absorption of a napkin in use, that is to say suspended vertically so that the fluid absorbed tends to reduce the absorption capacity of the napkin with respect to the hydrostatic pressure.

Each napkin is hence suspended vertically on a support and urine is poured on the upper portion of the napkin by means of a tube sending a pulsed jet of 30 ml in 5 seconds. This volume of 30 ml and this flow rate of 6 ml/s correspond to the average urological data of an infant of 9 months hence of weight about 9 kg.

To avoid the jet perforating the napkin, a piece of unwoven fabric is fixed at the point of impact and the urination operation (a jet of 30 ml in 5 seconds) is repeated every minute, until rupture under its own weight of the soaked napkin. The time of one minute is sufficient to insure complete distribution of the volume poured on each occasion.

The results are given in Table II below.

TABLE II

| | Effective Absorption in g/g | Remarks |
|---|---|---|
| Napkin of pure defibered woodpulp | 3.6 | The pads rupture before saturation |
| Napkin of defibered woodpulp with increase in the cohesion by a thermofusible glue: | | |
| N° 1 about 10 g/m² | 7.3 | The pads rupture at the limit of saturation |
| N° 2 about 20 g/m | 7.8 | |
| For an acrylic glue: about 10 g/m² | 6.3 | The pads do not rupture but are less saturated. |

These simple tests establish the fact that on wearing a napkin based on defibered woodpulp whose cohesion has not been increased by means of a binder, a degradation of the napkin frequently occurs when a certain level of saturation in absorption is reached whereas, in the case of napkins whose cohesion is increased with a binder, the degradation by rupture only occurs after saturation or even does not happen.

The effective overall absorption of the napkin with reinforced cohesion of the invention is greater than that of the prior art to the extent that there is better use of the absorbant mass of the napkin as a whole. Thus, for an equal effective absorption capacity, the napkins of the invention call upon a smaller absorbant mass than conventional napkins whose cohesion is not increased with a binder.

The invention hence enables the cohesion of napkins to be very substantially improved whether the latter are dry or wet. Better use of the absorbent mass available is made and there is not, on the one hand, degradation before the first urination and, on the other hand, less degradation between the first and the second urinations.

The napkins also preserve a correct appearance whether they are worn dry or wet.

We claim:

1. An absorbent article comprising a base sheet of fluid impervious material, a top sheet of fluid pervious non-woven material, said sheets being connected to each other about the periphery, and an absorbent pad disposed between said top sheet and said base sheet, said absorbent pad having a central portion and two side panels, said side panels being folded under said top sheet and over said central panel, and a binder on said central panel securing said side panels to said central panel to render said absorbent pad more absorbent, said absorbent pad including a wadding sheet, said binder penetrating said wadding sheet binding said side panels to said central panel.

2. An absorbent article according to claim 1, wherein said pad is of a wood fibrous material, said binder penetrating some of said fibers of said material.

3. An absorbent article according to claim 2, wherein said binder covers no more than 80% of said central panel.

4. An absorbent article according to claim 1, wherein said wadding sheet is in the form of an envelope.

* * * * *